United States Patent [19]

Russo

[11] Patent Number: 5,020,546
[45] Date of Patent: Jun. 4, 1991

[54] CASUALTY WRAP WITH INTEGRAL MEDICAL ACCESS CHAMBER

[75] Inventor: Anthony L. Russo, Lansdale, Pa.
[73] Assignee: Calspan Corporation, Buffalo, N.Y.
[21] Appl. No.: 481,547
[22] Filed: Feb. 20, 1990
[51] Int. Cl.[5] .............................................. A61B 19/00
[52] U.S. Cl. ................... 128/849; 128/873; 2/2; 600/21
[58] Field of Search ............ 2/2; 128/846, 849; 600/21; 27/28; 5/413, 82 R

[56] References Cited

U.S. PATENT DOCUMENTS

| | | | |
|---|---|---|---|
| 4,485,489 | 12/1984 | Pilie et al. | 2/2 |
| 4,485,490 | 12/1984 | Akers et al. | 2/2 |
| 4,485,534 | 12/1984 | Pilie et al. | 24/384 |
| 4,485,806 | 12/1984 | Akers | 128/873 X |
| 4,612,916 | 9/1986 | Akers et al. | 600/21 |

Primary Examiner—Robert A. Hafer
Assistant Examiner—Lynda M. Cofsky
Attorney, Agent, or Firm—Biebel, French & Nauman

[57] ABSTRACT

A litter bag is provided for isolating a casualty from a contaminated environment. The litter bag includes a collapsible access chamber mounted over an aperture in the bag whereby personnel may have immediate and direct access to the casualty. The access chamber is formed with tubular passages which may be filled with a gas to expand the chamber from a collapsed position to form a semi-rigid structure.

21 Claims, 5 Drawing Sheets

CASUALTY WRAP WITH INTEGRAL MEDICAL ACCESS CHAMBER

BACKGROUND OF THE INVENTION

This invention relates generally to the medical treatment of casualties and particularly to the medical treatment of casualties located in a contaminated environment.

Typically, when a person is injured and becomes a casualty in a contaminated environment, such as occurs in a chemical warfare confrontation, the casualty is placed within a litter bag or enclosure for transportation to a medical facility. The enclosure is manufactured of a material that inhibits or prevents the transfer of contaminants from the ambient environment to the casualty.

In many cases, it is imperative that medical treatment be given to the casualty immediately, however, in order to administer treatment, the litter bag with its casualty must first be transported into an enclosure within which medical personnel may work on the casualty or additional means must be provided for allowing access to the casualty without introducing contaminants into the enclosure containing the casualty. The apparatus currently available for treating the casualty in the field is subject to the problem of the treatment being delayed by the transportation of the casualty as well as the problem of the possible unavailability of medical facilities or unavailability of the needed additional apparatus to ensure that the casualty is protected from contaminants.

U.S. Pat. No. 4,485,806 to Akers and assigned to the assignee of this application, discloses a prior art evacuation apparatus for removing a casualty in a litter bag or enclosure to a treatment facility. This device is subject to the limitation of a treatment facility being available for use with the enclosure containing the casualty. Further, the access of the medical personnel to the casualty is limited since they must operate with their hands within gloves attached to the enclosure containing the casualty.

U.S. Pat. Nos. 4,612,916 and 4,485,490 both to Akers et al and both assigned to the assignee of this application, disclose a method and apparatus for treating the casualty located within a contaminated area by use of a glove box attached to the enclosure containing the casualty. While the means for treating the casualty does not require that the casualty be transported to a medical facility or a treatment enclosure, the glove box is somewhat bulky, and the treatment of the casualty is subject to the availability of a glove box at the site of the casualty. In addition, the glove box requires the medical personnel to work with their hands within not only their own protective gloves but also within gloves attached to the glove box such that the tactile sensitivity of the worker's hands in working on the casualty is reduced.

Thus, there is a need for an enclosure for protecting the casualty within a contaminated environment which also provides medical personnel with convenient access for rendering immediate treatment. There is also a need for an enclosure which provides medical personnel with direct access to the casualty without introducing contaminants into the enclosure containing the casualty.

SUMMARY OF THE INVENTION

In accordance with the present invention, a treatment apparatus is provided for allowing direct access to a casualty located within an enclosure for isolating the casualty from a contaminated environment. The treatment apparatus comprises a litter bag or enclosure and an access chamber attached to an upper horizontal surface of the litter bag. The access chamber is positioned over an aperture formed in the litter bag such that the interior of the access chamber is in communication with the interior of the litter bag.

In a preferred embodiment of the invention, the access chamber is provided with four vertical side walls and an upper panel having a transparent window through which medical personnel may view the casualty. One of the vertical walls includes a substantially vertically oriented elongated opening with a fastener system attached thereto for providing access to the interior of the chamber. The fastener system is operable to open and close the opening in the access chamber and is designed to be compatible with a similar fastener on an enclosure containing a person administering medical treatment.

Also in the preferred embodiment, the vertical walls of the access chamber are formed of a flexible material and the edges joining the vertical side walls to one another and to the upper panel are provided with means defining tubular gas passages therein for receiving pressurized gas, and means are provided for connecting the tubular gas passages to a pressurized gas source.

When the tubular gas passages are filled with a pressurized gas, the edges of the access chamber form a semi-rigid parallelepiped structure such that the side walls are flat and are brought to a vertical position, and the upper panel is located distal from the lower portion of the access chamber. When the pressurized gas is released from the tubular gas passages the vertical walls of the chamber may be collapsed and folded upon themselves to a position wherein the upper panel is in a location adjacent to the lower portion of the chamber.

Thus, a litter bag is provided which differs from prior art litter bags in that, when immediate medical treatment is required, the access chamber located on the bag may be expanded by filling the tubular gas passages from a gas source, for example a hand pump or an aerosol canister, such that the chamber expands and the medical personnel have direct and ready access to the casualty through the opening in the side of the access chamber.

In an alternative embodiment the litter bag is provided with a removable panel which may be interchanged with the access chamber such that the access chamber may be selectively attached to particular litter bags which are anticipated to be used for casualties requiring immediate medical treatment.

Other objects and advantages of the invention will be apparent from the following description, the accompanying drawings, and the appended claims.

DETAILED DESCRIPTION OF THE PREFERRED EMBODIMENT

Figure 1:
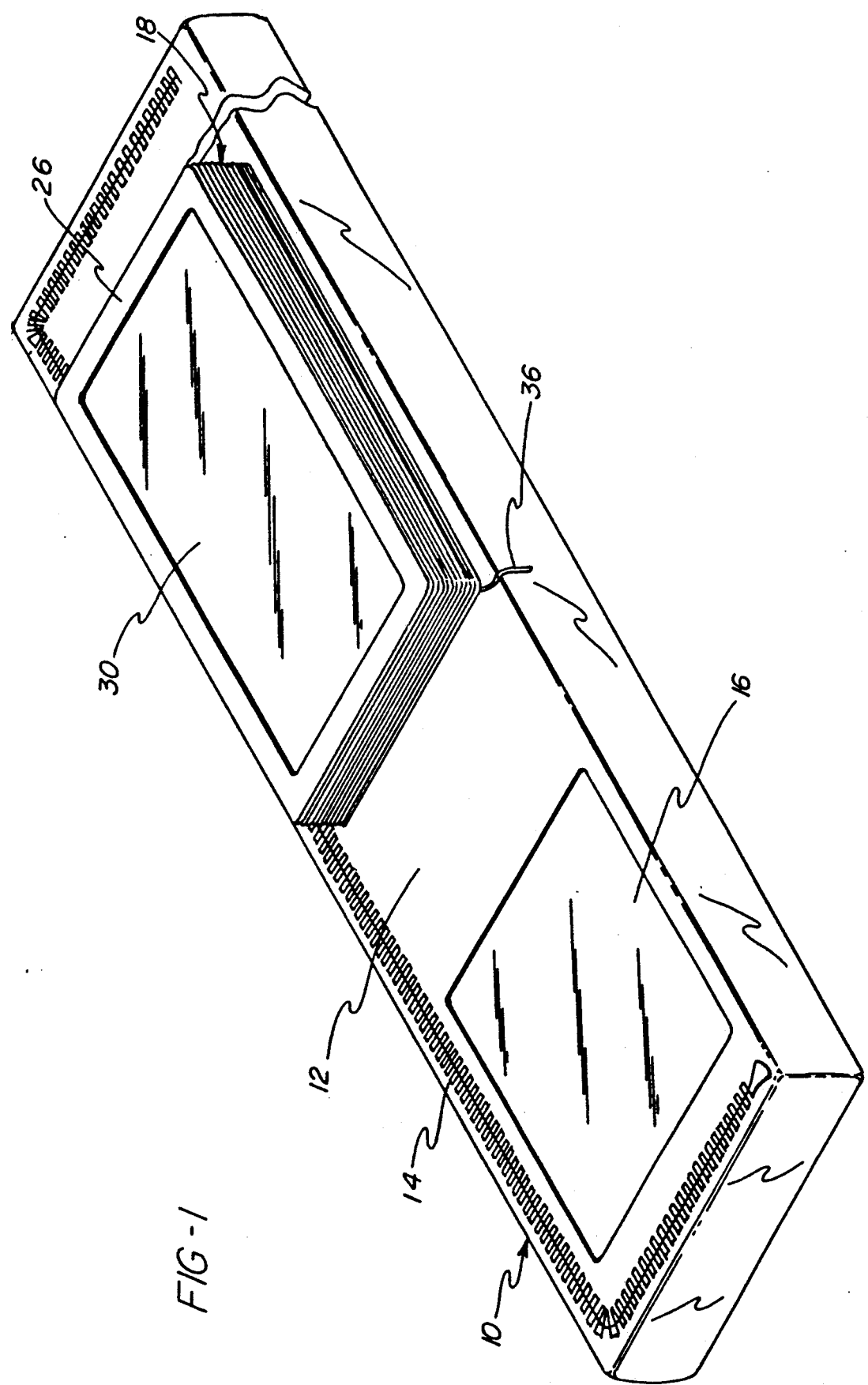
FIG. 1 is a perspective view of the litter bag of the present invention with the access chamber collapsed.

Referring to FIG. 1, it can be seen that an enclosure or litter bag 10 is provided having a conventional envelope-like structure. The litter bag 10 has an upper horizontal and substantially planar flexible panel 12 and an elongated opening and fastener means 14 formed along substantially the entire length of the litter bag 10 as well as extending along a portion of each of the ends of the bag 10 to form a C-shaped opening, the size and shape of the elongated opening and fastener means 14 being selected so as to facilitate insertion of a casualty into the litter bag 10. The fastener means 14 may be a conventional zipper type fastener system or, alternatively, may be of the form disclosed in U.S. Pat. No. 4,485,534 which is incorporated herein by reference and wherein opposing panels may be attached to each other by fasteners provided for opening and closing openings in each of the panels.

A transparent panel 16 is positioned at one end of the panel 12 for permitting the casualty to view out of the litter bag 10, and a medical access chamber 18 is positioned approximately centrally on the surface of the panel 12 at its other end. The access chamber 18 is positioned over an aperture 19 formed in the panel 12 (see FIG. 5) such that the interior of the access chamber 18 is in communication with the interior of the litter bag 10.

Figure 2:
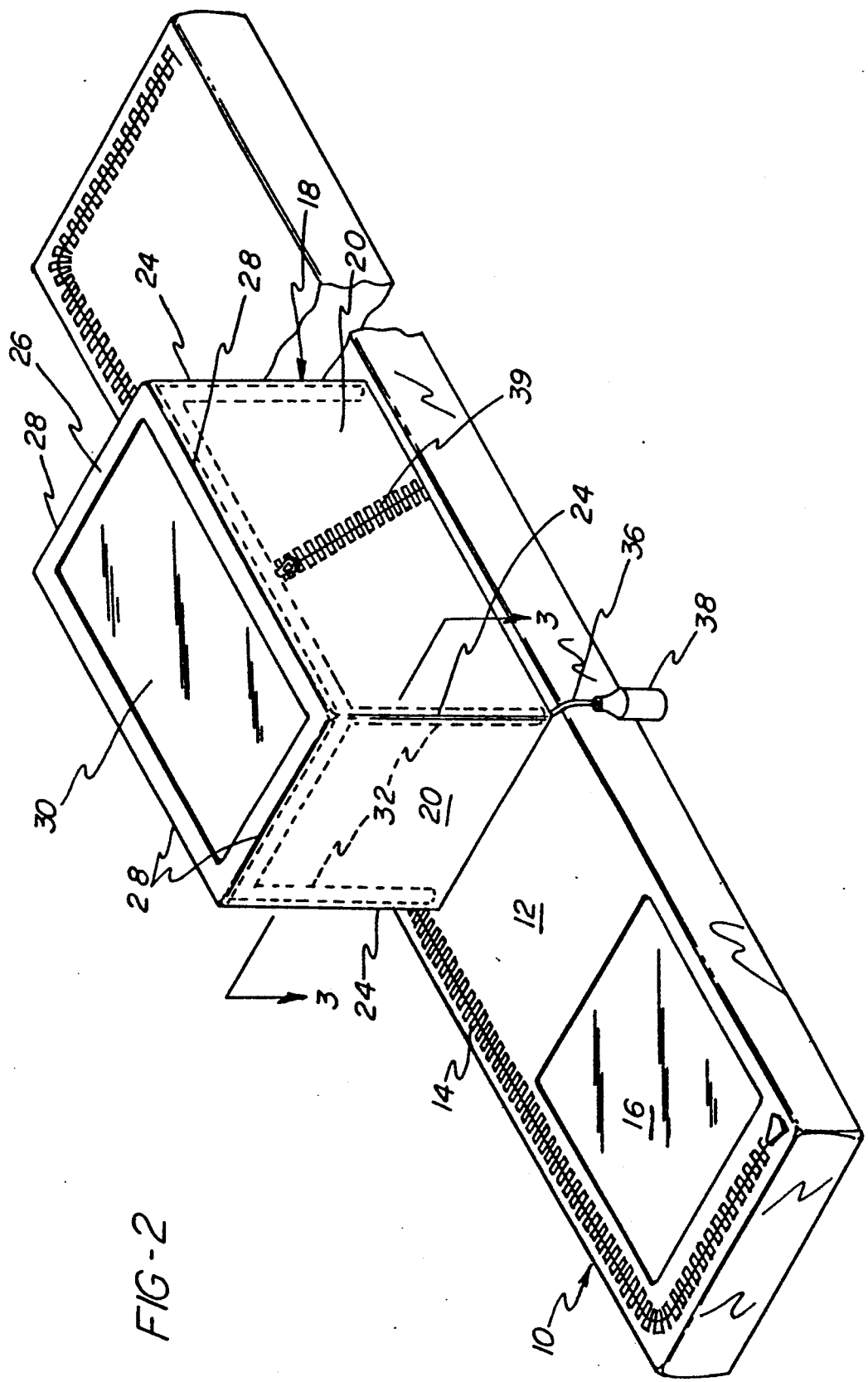
FIG. 2 is a perspective view of a litter bag of the present invention with the access chamber expanded.

Referring to FIGS. 1 and 2, the access chamber 18 is formed as a collapsible structure which has a compact form when not in use and which can be expanded for use, as depicted in FIG. 2. The access chamber 18 has four vertical side walls 20 formed of a flexible material which may fold down into "accordion folds", as shown in FIG. 1, and which are attached to and oriented substantially perpendicular to the horizontal planar surface 12. The vertical walls 20 are joined to one another by vertical edges 24 and are attached to a horizontal panel 26 along horizontal edges 28. The horizontal panel 26 is provided with a transparent window 30 for allowing medical personnel to view into the chamber 18 when administering medical treatment.

The access chamber 18 is preferably formed integrally with the litter bag 10 and thus it is readily available whenever medical treatment is required. When the chamber 18 is needed for administering medical treatment, the vertical walls 20 may be readily expanded through use of means formed in the vertical and horizontal edges 24, 28.

Figure 3:
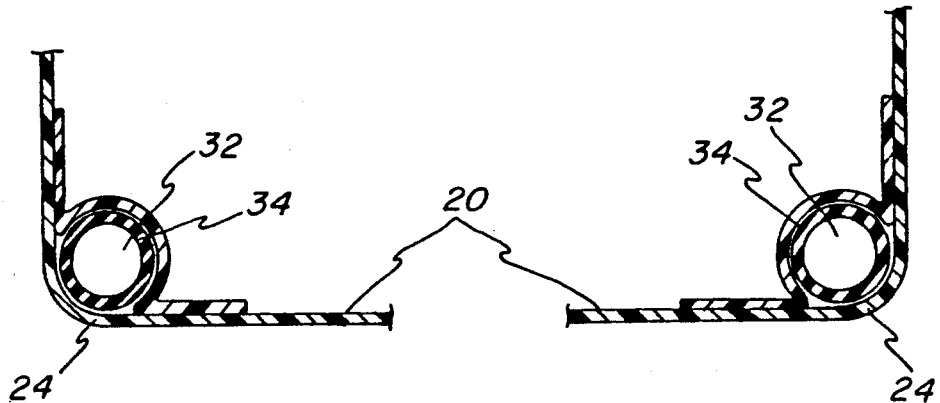
FIG. 3 is a view taken on section 3—3 of FIG. 2 showing one of the vertical side walls of the chamber and the tubular gas passages formed along the edges.

In accordance with the invention, and with particular reference to FIGS. 2 and 3, the vertical and horizontal edges 24, 28 of the access chamber 18 are formed with tubular gas passages 32 which essentially form a parallelepiped structure. As may be best seen in FIG. 3, the gas passages 32 may be formed by flexible inner tubes 34 which are encased within the material of the walls 20. The wall material may be formed out of a flexible plastic material which may be either heat sealed or sewn around the inner tubes 34, and is preferably formed of a material which is impermeable to any contaminants which are expected to be found in the environment in which the litter bag 10 and access chamber 18 are to be used.

The tubular gas passages 32 may be alternatively formed integrally with the walls of the access chamber 18. In this case, the access chamber walls 20 must be formed of a material which is impermeable to the pressurized gas used to fill the gas passages 32.

The gas passages 32 are provided with means 36 for connection to a source 38 of pressurized gas. Any conventional pressurized gas source 38 may be provided, for example, an aerosol canister or a hand pump. Upon applying a pressurized gas source 38 to the means 36 for connecting the source 38 to the tubular gas passages 32, the access chamber 18 moves from the position shown in FIG. 1, in which the side walls 20 are folded down upon themselves and the upper panel 26 is in a location adjacent to the lower portion of the access chamber 18, to a position in which the upper panel 26 is distal from the lower portion of the access chamber 18 and the side walls 20 are formed as substantially planar surfaces, as shown in FIG. 2.

Figure 4:
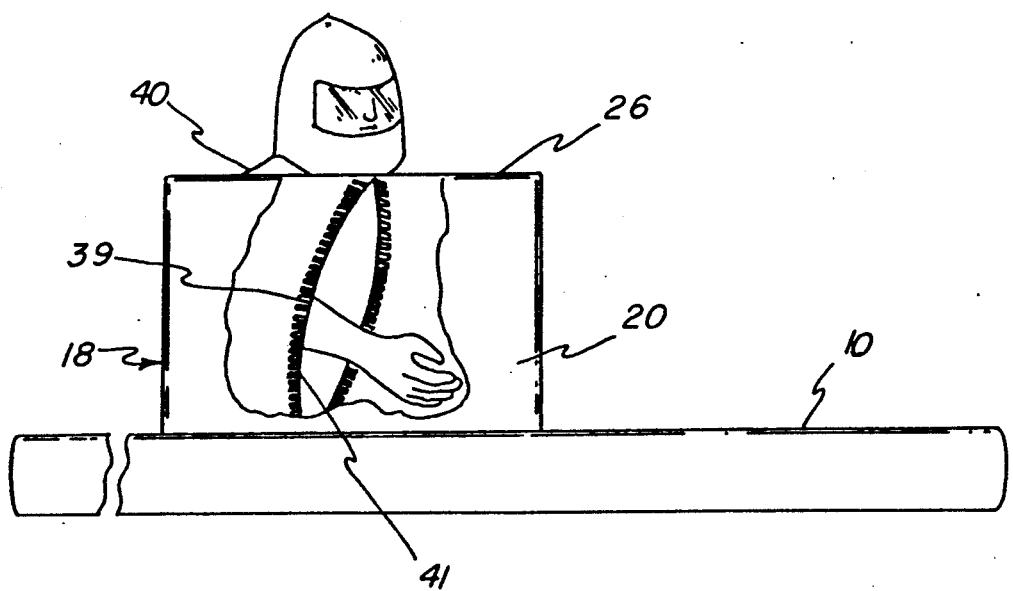
FIG. 4 is an elevational view with a wall of the chamber cut away to show the connection between the chamber and an enclosure for a person giving medical treatment.

When the access chamber 18 is in the position shown in FIG. 2 with the walls 20 positioned vertically relative to the horizontal panel 12 of the litter bag 10, an opening having a fastener means 39 attached thereto is exposed for connection to a second enclosure 40 (FIG. 4). The second enclosure 40 is provided for protecting a person administering medical treatment from the contaminated environment. The enclosure 40 is preferably provided with an elongated opening and a fastener means 41 attached thereto which is compatible with the fastener means 39 located on the wall 20 of the access chamber 18. The fasteners 39, 41 and associated slide member are preferably of the form disclosed in U.S. Pat. No. 4,485,534 and described above in reference to fastener means 14.

Thus, the fastener means 39 may be joined to the fastener means 41 as the elongated openings in the access chamber 18 and the enclosure 40 are simultaneously opened such that a person within the enclosure 40 may have direct access into the access chamber 18 and thus into the litter bag 10 through the aperture 19. It should be noted that although only one slider for the fastener means 39 is shown positioned for sliding downward to open the chamber 18 in FIG. 2, an additional slider may be positioned at the bottom of the fastener means 39 which may be slid upward to open the chamber 18, such that the fastener means 39 may be operated in either direction when attaching the enclosure 40 to the chamber 18.

In a typical use of the access chamber 18, the litter bag 10 containing the casualty may be placed on a table such that the bottom of the chamber 18 is approximately waist high to medical personnel operating on the casualty. In addition, the access chamber 18 may extend upward to approximately shoulder height of the medical personnel such that when the enclosure 40 containing a medic is attached to the chamber 18, the medic may easily reach into the chamber 18 to operate on the casualty while also being able to view into the chamber 18 through the transparent panel 30 as treatment is being administered.

Further, by providing a litter bag 10 which has an access chamber 18 with flexible walls 20 which are collapsible, means are provided for treating a casualty without substantially increasing the bulk of the litter bag 10. In addition, by providing the bag 10 with an access chamber 18 already attached when the casualty is placed within the bag 10, the inconvenience and delay associated with trying to attach a flexible chamber to a litter bag is avoided.

Figure 5:
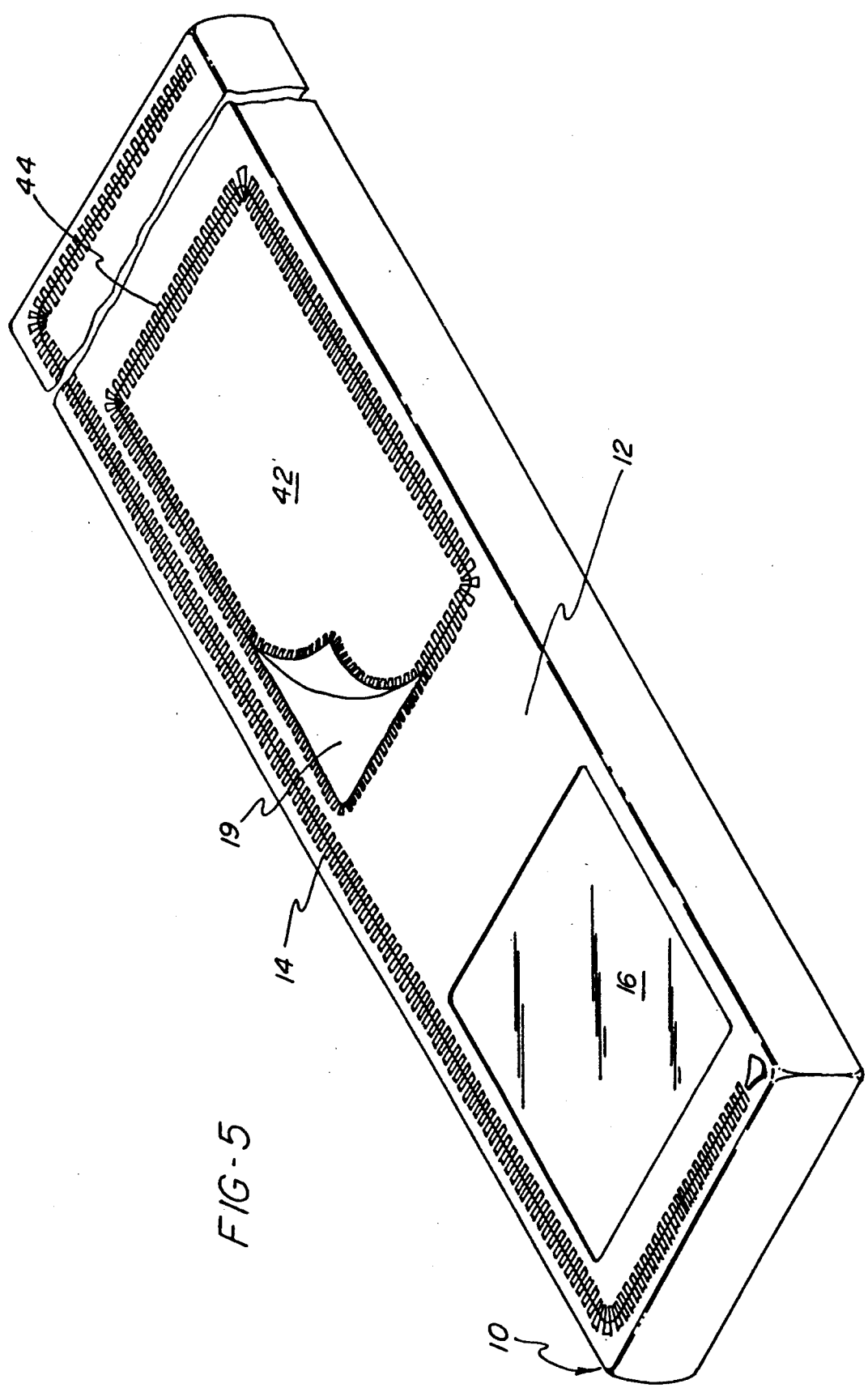
FIG. 5 is a perspective view of another embodiment showing a removable panel attached to the litter bag to cover the aperture for the access chamber.

An alternative embodiment of the present invention is shown in FIG. 5, in which the access chamber 18 is removable from the litter bag 10 and a removable flap 42 is provided for covering the aperture 19 in the litter bag 10. In this case, a fastener means 44 is provided, which may be a conventional zipper type system or may be of the type disclosed in U.S. Pat. No. 4,485,534, and which is compatible with fasteners on the bottom of the access chamber 18 and the removable flap 42. Thus, a group of litter bags 10 provided with removable flaps 42 may be stored until needed and access chambers 18 may be attached to the litter bags 10 selectively as casualties needing immediate treatment are anticipated.

Figure 6:
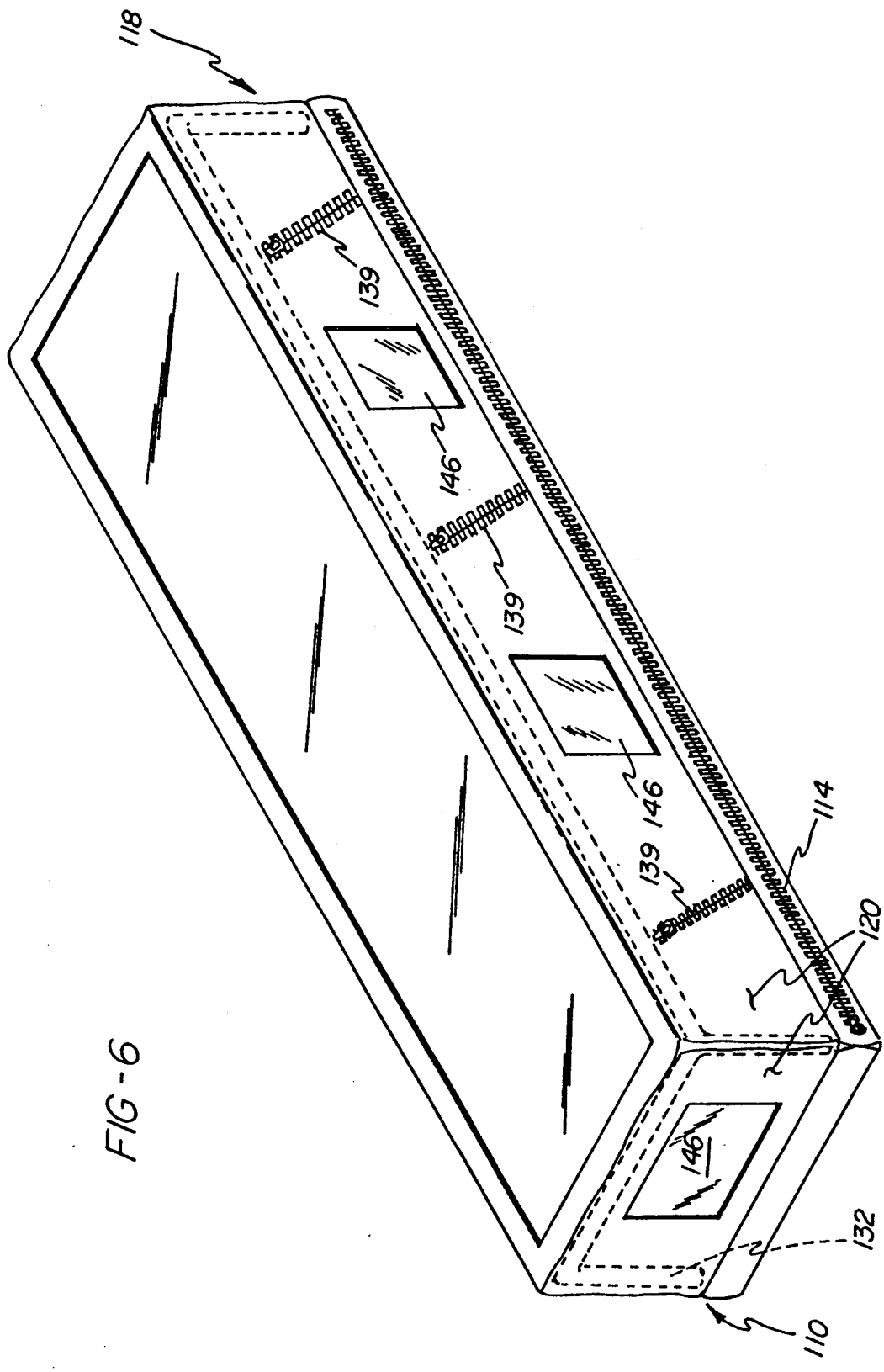
FIG. 6 is a perspective view of another embodiment in which the access chamber dimensionally corresponds to the litter bag in plan view.

In another embodiment of the present invention, as shown in FIG. 6, the collapsible access chamber 118 is formed with gas passages 132 similar to the previous embodiments and the chamber 118 may be formed with the same dimensions in a plan view as the dimensions of the litter bag 110 such that the sides 120 of the access chamber 118 form a continuation of and are substantially coplanar with the sides of the litter bag 110. Also, additional fastener means 139 of the type disclosed in U.S. Pat. No. 4,485,534 may be provided such that medical personnel may have access to the casualty along the entire length of the litter bag 110. In addition, the top panel 126 may be provided with a transparent window 130 and portions of the sides 120 of the access chamber 118 may be formed with transparent panels 146 to improve visibility into the chamber 118. In this embodiment the elongated opening and fastener means 114 for receiving a casualty into the bag 110 will be positioned on the side of the bag 110 below the chamber 118.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. An apparatus for providing medical treatment to a casualty including a first enclosure for isolating a casualty from a contaminated environment;
   a flexible access chamber attached to said first enclosure;
   said access chamber being formed as a collapsible structure including a flexible wall portion adapted to assume a first expanded position when said access chamber is in use for providing access to said casualty in said first enclosure;
   said access chamber being adapted to assume a second collapsed position when said access chamber is not in use; and
   said flexible wall portion including passage means for receiving a pressurized fluid such that when said passage means is supplied with a pressurized fluid, said access chamber moves from said collapsed to said expanded position to form a semi-rigid structure.

2. The apparatus of claim 1 wherein said flexible wall portion of said access chamber includes a plurality of flexible walls joined at a plurality of edges and said passage means includes means in said edges defining tubular gas passages for receiving a pressurized gas.

3. The apparatus of claim 2 wherein said walls fold down upon themselves to form "accordion folds" in said collapsed position and said walls are substantially planar in said expanded position.

4. The apparatus of claim 3 wherein said first enclosure includes at least one substantially planar surface and said access chamber includes at least one vertical wall oriented substantially perpendicular to said substantially planar surface when said access chamber is in said expanded position.

5. The apparatus of claim 4 wherein said vertical wall includes means defining a first opening formed therein, and a first fastener means operable for opening and closing said first opening.

6. The apparatus of claim 5 wherein said first opening is elongated and oriented substantially perpendicular to said substantially planar surface.

7. The apparatus of claim 6 wherein a second enclosure is provided for containing a person, said second enclosure having means defining a second opening and a second fastener means attached thereto compatible with said first fastener means such that as said first fastener means is operated to open said first opening, said second fastener means may become sealingly engaged with said first fastener means, thereby placing the interior of said second enclosure in direct communication with the interior of said access chamber.

8. The apparatus of claim 7 wherein said first enclosure includes means defining a third opening for receiving said casualty and a fastener attached thereto operable for opening and closing said third opening.

9. The apparatus of claim 6 wherein said access chamber includes a panel having a transparent window, said panel being attached to said walls.

10. The apparatus of claim 9 wherein said first enclosure includes a transparent window through which said casualty may see out of said enclosure.

11. The apparatus of claim 2 wherein said access chamber is formed of a gas impermeable material and said gas passages are formed by said material forming said walls.

12. The apparatus of claim 2 wherein said gas passages are formed by flexible tubes attached within said edges of said access chamber.

13. The apparatus of claim 3 wherein said first enclosure is formed with side portions and said walls of said access chamber are substantially coplanar with said side portions.

14. The apparatus of claim 13 wherein said access chamber includes a plurality of elongated openings formed in a wall thereof and fastener means for opening and closing said openings.

15. The apparatus of claim 14 wherein said access chamber includes a substantially horizontal panel, and a plurality of transparent panels are attached to said walls and to said substantially horizontal panel to permit said casualty to be viewed from different positions around said access chamber.

16. The apparatus of claim 4 wherein said access chamber may be attached to and detached from said substantially planar surface of said first enclosure.

17. The apparatus of claim 16 wherein said substantially planar surface of said first enclosure includes means defining an aperture therein and a removable panel which may be attached to said planar surface at said aperture interchangeably with said access chamber.

18. An apparatus for providing medical treatment to a casualty including an enclosure for isolating a casualty from a contaminated environment, said enclosure having at least one substantially planar surface;
   means defining an aperture in said substantially planar surface;
   an access chamber including a flexible wall portion attached in sealing engagement to said substantially planar surface of said enclosure and positioned over said aperture;
   said access chamber including at least one vertical wall oriented substantially perpendicular to said substantially planar surface;
   means defining a first opening in said vertical wall;
   a first fastener means attached to said first opening operable for opening and closing said opening;
   a second enclosure for containing a person and means defining a second opening therein;
   second fastener means attached to said second opening, said second fastener means being compatible with said first fastener means such that as said first fastener means is operated to open said first opening, said second fastener means may become sealingly engaged with said first fastener means to place the interior of said access chamber in communication with the interior of said second enclosure; and
   said flexible wall portion including passage means for receiving a pressurized fluid such that when said passage means is supplied with a pressurized fluid, said access chamber moves from a collapsed position wherein said flexible wall portion is folded down upon itself to an expanded position wherein said access chamber is formed as a semi-rigid structure.

19. The apparatus of claim 18 wherein said first opening is elongated and oriented substantially perpendicular to said substantially planar surface.

20. The apparatus of claim 18 wherein said flexible wall portion of said access chamber includes a plurality of flexible walls joined at a plurality of edges, said passage mans includes means in said edges defining tubular gas passages for receiving a pressurized gas, such that said access chamber assumes said expanded position wherein said walls are substantially planar and a semi-rigid structure is formed when said gas passages receive said pressurized gas, and said access chamber assumes said collapsed position wherein said walls are folded down upon themselves when said pressurized gas is released from said gas passages.

21. A casualty wrap for isolating a casualty from a contaminated environment, said casualty wrap comprising:
   a litter bag having at least one substantially planar horizontal elongated flexible panel;
   means defining a first elongated opening on said flexible panel with a first fastener means attached thereto and operable to open and close said first opening, said first opening being sized to receive a casualty therethrough;
   a transparent panel located at one end of said flexible panel for permitting said casualty to view out of said litter bag;
   means defining a substantially rectangular opening located approximately centrally on said flexible panel;
   an access chamber for providing access to said casualty in said litter bag for medical treatment of said casualty;
   said access chamber having four collapsible vertical walls joined at vertical edges, an upper panel having a transparent window joined to said vertical walls at horizontal edges, and an open lower portion sealed to said litter bag around the periphery of said substantially rectangular opening such that the interior of said access chamber is continuous with the interior of said litter bag;
   said horizontal and vertical edges having means defining tubular gas passages therein for receiving a pressurized gas and means for connecting said tubular gas passages to a pressurized gas source; and
   means defining a second elongated opening formed in one of said vertical walls with a second fastener means attached thereto operable to open and close said second opening,
   a second enclosure for containing a person and means defining a third elongated opening therein;
   third fastener means attached to said third opening, said third fastener means being compatible with said second fastener means such that as said second fastener means is operated to open said second opening, said third fastener means may become sealingly engaged with said second fastener means to place the interior of said access chamber in communication with the interior of said second enclosure;
   said vertical walls of said access chamber being collapsible to position said upper panel in a location adjacent to said lower portion of said access chamber, and said vertical walls and tubular gas passages forming a semi-rigid parallelepiped structure with said upper panel located distal from said lower portion when said tubular gas passages contain a pressurized gas.

* * * * *